United States Patent [19]
Takahashi et al.

[11] Patent Number: 5,902,230
[45] Date of Patent: May 11, 1999

[54] ELECTRONIC ENDOSCOPE SYSTEM WITH INFORMATION COMBINED IN DIGITAL OUTPUT

[75] Inventors: Akihiro Takahashi; Kohei Iketani, both of Tokyo, Japan

[73] Assignee: Asahi Kogaku Kogyo Kabushiki Kaisha, Tokyo, Japan

[21] Appl. No.: 08/596,723

[22] Filed: Feb. 5, 1996

[30] Foreign Application Priority Data

Feb. 6, 1995 [JP] Japan .................................. 7-017585
Jun. 22, 1995 [JP] Japan .................................. 7-155835

[51] Int. Cl.[6] .............................................. A61B 1/045
[52] U.S. Cl. ............................................. 600/109; 348/76
[58] Field of Search .................................. 600/109, 117, 600/118, 134, 921; 348/65, 71, 74, 76

[56] References Cited

U.S. PATENT DOCUMENTS

| | | | |
|---|---|---|---|
| 4,998,972 | 3/1991 | Chin et al. | 348/65 |
| 5,111,306 | 5/1992 | Kanno et al. | 348/74 |
| 5,124,789 | 6/1992 | Hiyama et al. | 348/74 |
| 5,305,098 | 4/1994 | Matsunaka et al. | 348/65 |
| 5,361,203 | 11/1994 | Hiyama et al. | 364/413.13 |
| 5,374,965 | 12/1994 | Kanno | 348/71 |
| 5,583,566 | 12/1996 | Kanno et al. | 600/109 |
| 5,594,497 | 1/1997 | Ahern et al. | 348/71 |

FOREIGN PATENT DOCUMENTS 5176883  7/1993  Japan .................................. 600/118

Primary Examiner—John R. Leubecker
Attorney, Agent, or Firm—Greenblum & Bernstein, P.L.C.

[57] ABSTRACT

An electronic endoscope system which includes a device for detecting an image, and a device for inputting an information signal. The image detecting device outputs an electrical image signal, which is converted to an analog video signal and a digital video signal. The digital video signal is combined with the information signal by an image combining device, to form a digital information signal. The digital information signal is serially outputted to a device which displays the image data in accordance with the outputted serial digital information signal. The digital information signal is also serially outputted to a device which reproduces the information signal in accordance with the outputted serial digital information signal.

23 Claims, 15 Drawing Sheets

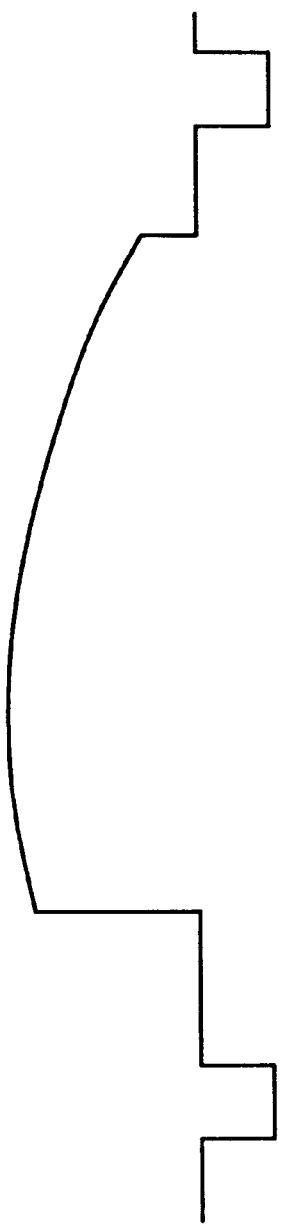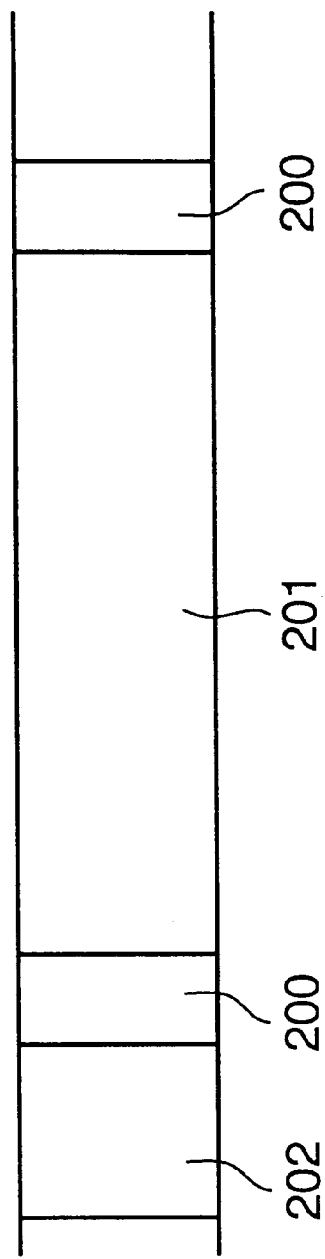
FIG. 4A
FIG. 4B

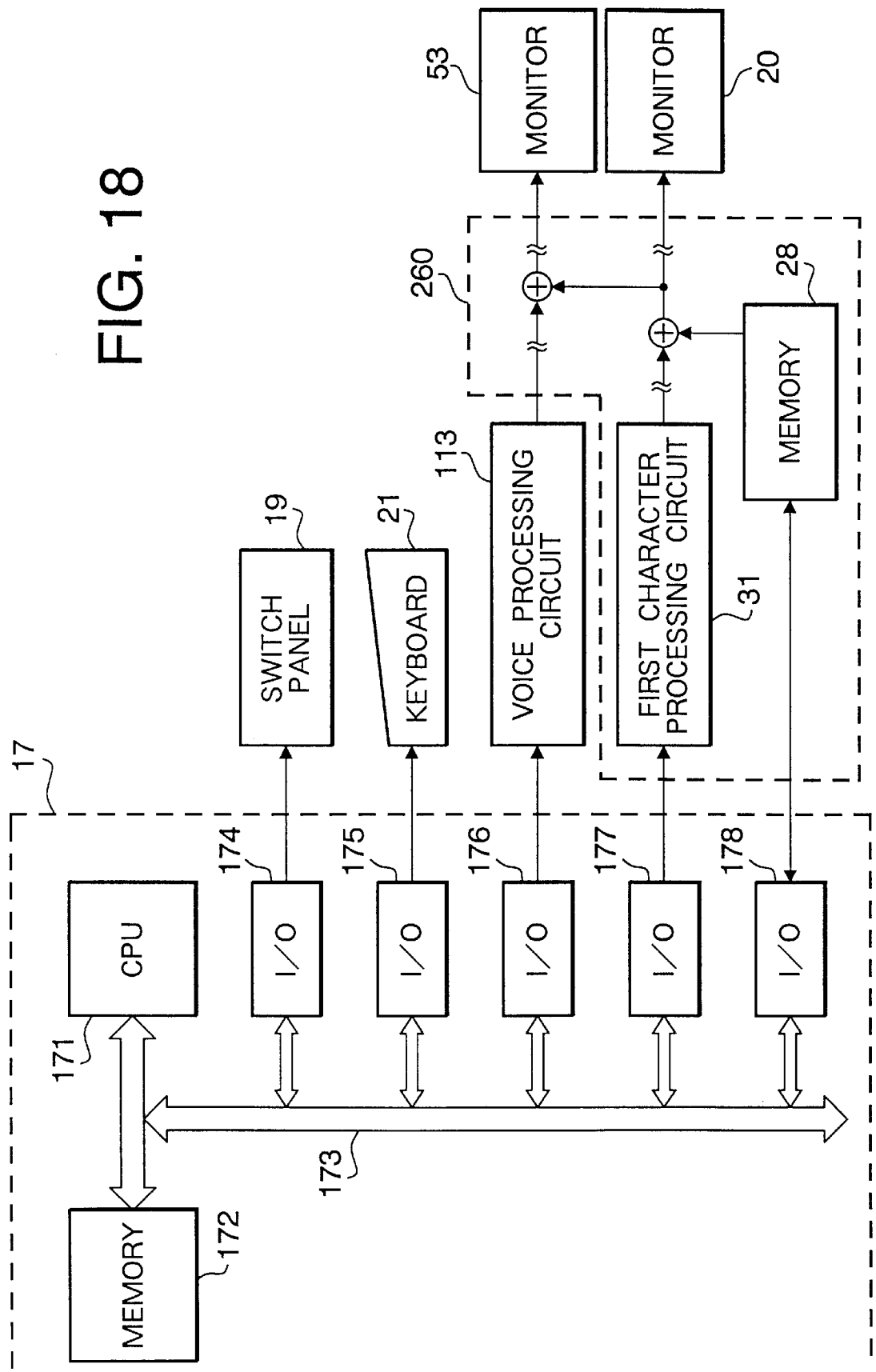

ELECTRONIC ENDOSCOPE SYSTEM WITH INFORMATION COMBINED IN DIGITAL OUTPUT

BACKGROUND OF THE INVENTION

The present invention relates to an electronic endoscope system which detects an image of an object using an imaging device, processes the detected image, and outputs the processed image to a monitor for viewing.

In the conventional electronic endoscope system, an image of an object (such as internal organ or tract of the human body) is formed by an optical system on an imaging device, such as a CCD. The imaging device outputs an electrical signal to a video processor. The video processor processes the signals and outputs an analog RGB signal, a composite video signal and an S video signal. The composite video signal and S video signal are then inputted to a monitor in order to display the image detected by the electronic endoscope system.

Recently, for medical studies, there has been a need to remotely observe images detected by an electronic endoscope system, in real time. If the conventional electronic endoscope system is employed, the analog video signals output by the video processor must be transmitted to the monitor at the remote location. If the distance of the remote location from the electronic endoscope system is great, then due to transmission loss, the quality of the image displayed on the monitor will degrade to an unacceptable level.

Further, in the conventional electronic endoscope system, information related to the name of the patient, the current date and time, and comments by the medical personnel are displayed on the monitor. However, data related to an operation of the electronic endoscope system and data related to the type of image processing are only indicated on the video processor. Therefore, if the image is being observed on a monitor at a remote location, it is not possible to display all the information related to the current status of the electronic endoscope system.

SUMMARY OF THE INVENTION

It is therefore an object of the present invention to provide an improved electronic endoscope system which is capable of displaying a high quality image on a monitor located at a remote location.

It is another object of the present invention to provide an improved electronic endoscope system which can transmit all necessary information related to a function and/or operation of the electronic endoscope system to be displayed on a monitor at a remote location.

It is a further object of the present invention to provide an improved electronic endoscope system which can transmit an information signal, such as an audio signal, along with the observed image, to a monitor at a remote location.

According to a first aspect of the present invention, there is provided an electronic endoscope system which includes a device for detecting an image, and a device for inputting an information signal. The image detecting device outputs an electrical image signal, which is converted to a analog video signal and a digital video signal. The digital video signal is combined with the information signal by an image combining device, to form a digital information signal. The digital information signal is serially output to a device which displays the image data in accordance with the outputted serial digital information signal. The digital information signal is also serially outputted to a device which reproduces the information signal in accordance with the outputted serial digital information signal.

Therefore, the serially transmitted digital information signal can be sent to a remote location using a cable having a single line. Since the digital signal is transmitted, the loss of image quality can be avoided, and further the distance of the image displaying device (such as a remote monitor) from the electronic endoscope system, can be increased.

In one preferred embodiment, the information signal is a data signal related to an operation of the image combining device (such as video processor). Therefore, the operating condition of the image combining device can be transmitted to the remote location, and reproduced on the image displaying device.

In another preferred embodiment, the information signal is an analog audio signal such as a voice signal which is inputted using a microphone. The analog audio signal is digitized and multiplexed with the digital video signal to form the digital information signal. The digital information signal is then transmitted serially to an external monitor where the image and audio signals are reproduced. Therefore, verbal instructions can be given from the location of the electronic endoscope system to the location of the remote monitor.

Optionally, the digital information signal may be converted to an optical signal and transmitted using an optical fiber to the image displaying device.

According to a second aspect of the present invention, there is a provided an electronic endoscope system which includes a device for detecting an image, the image detecting device outputting an electrical image signal, and a device for converting the electrical image signal to an analog video signal and a digital video signal. The analog video signal is outputted to a first display device, and the digital video signal is serially outputted to a second display device.

The first display device may be located near the electronic endoscope system while the second display device is at a remote location. Therefore, by transmitting serial digital video data to the second display device, the distance of the second display device from the electronic endoscope system may be increased without any loss in image quality. The analog video signal which is outputted to the first display device includes a composite video signal and an S video signal.

Optionally, the electronic endoscope system further includes a device for processing character data and device for combining the character data with the analog video signal. Thus, the character data can be displayed along with the image signal on the first and second display devices. In a preferred embodiment, the character data includes data such as a current date and time, a name of a patient, and other comments that are to be added.

Further optionally, the electronic endoscope system includes a keyboard for inputting the character data.

According to a third aspect of the present invention, there is provided an electronic endoscope system wherein an image detected by an imaging device is separated into analog red, green and blue image signals, and the analog red, green and blue image signals are further processed and outputted to a monitor. The electronic endoscope system includes a device for outputting an analog composite video signal and an S video signal to the monitor, and a device for converting the analog red, green and blue image signals into a digital video signal. The digital video signal is then serially outputted to the monitor.

According to a fourth aspect of the present invention, there is provided an electronic endoscope system including:

a device for detecting an image, the image detecting device outputting an electrical image signal;

a devices for converting the electrical image signal to an analog video signal and a digital video signal;

a device for converting an analog audio signal to a digital audio signal;

a device for combining the digital video signal with the digital audio signal, to form a digital information signal;

a device for serially outputting the digital information signal;

a device for displaying the image data in accordance with the outputted serial digital information signal; and a device for reproducing the analog audio signal in accordance with the outputted serial digital information signal.

BRIEF DESCRIPTION OF THE DRAWINGS

FIG. 4A shows a timing diagram of a transmission of an analog image from the video processor shown in FIG. 2 to a local monitor;

FIG. 4B shows a timing diagram of a transmission of serial image data from the video processor shown in FIG. 2 to a remote monitor;

FIG. 18 shows a block diagram of a system controller used in the video processor shown in FIG. 12.

DESCRIPTION OF THE PREFERRED EMBODIMENTS

Figure 1:
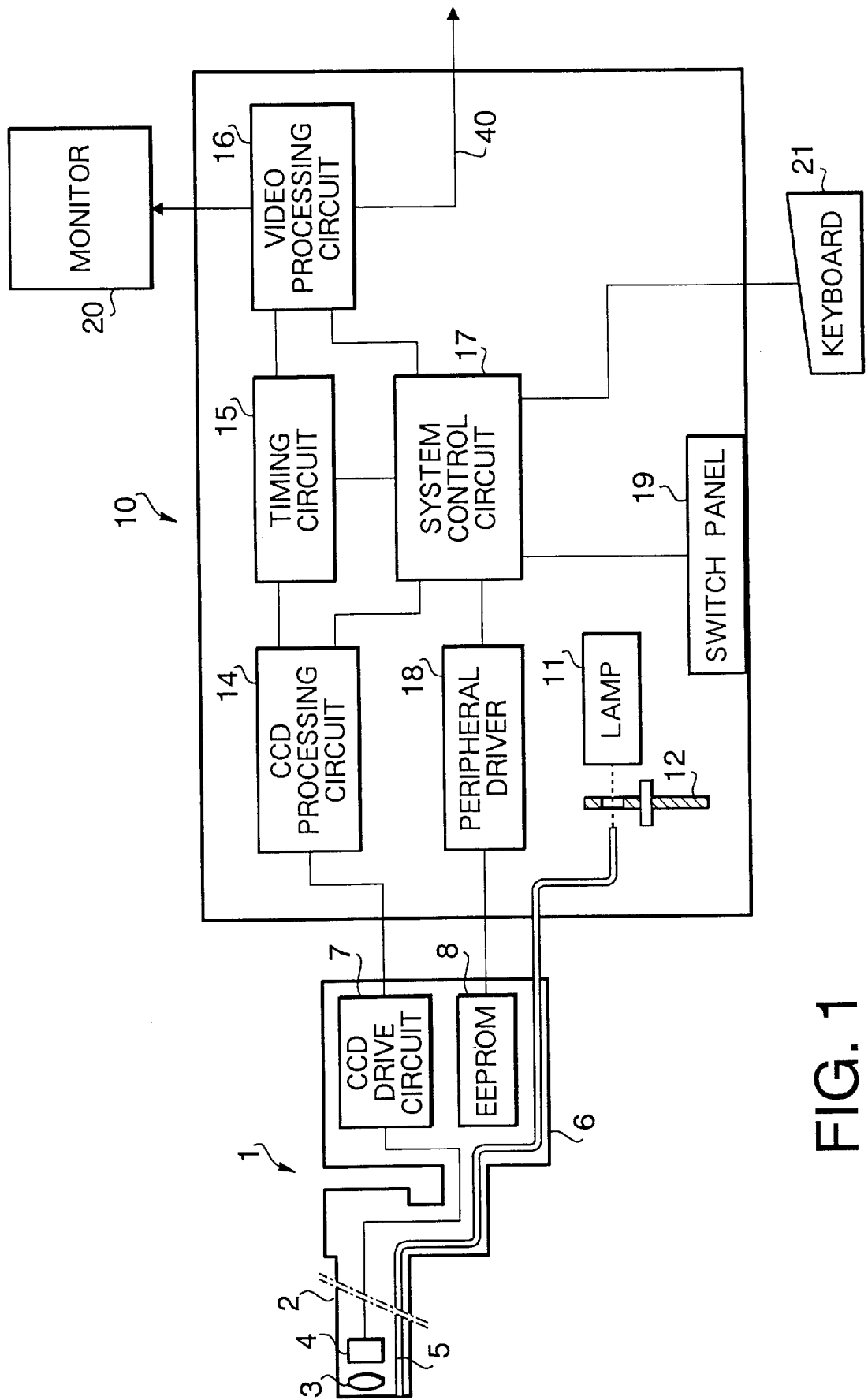
FIG. 1 shows a schematic diagram of a electronic endoscope system which embodies the present invention.

FIG. 1 shows a schematic diagram of an electronic endoscope system which embodies the present invention. The electronic endoscope system includes an endoscope 1 and an image processor 10. The endoscope 1 has an insertion portion 2 which is inserted into a cavity such as a digestive or respiratory tract of a hum body. An image forming lens 3 forms an image of an object on an imaging device, such as a CCD 4. The CCD 4 outputs an electrical signal to a CCD drive circuit 7. The CCD drive circuit 7 amplifies the signal and outputs the amplified signal to a CCD processing circuit 14 of the image processor 10.

A lamp 11 provides light to a fiber optic cable 5 via a filter 12 in order to illuminate the object to be viewed. The filter 12 is disk shaped and has a red colored filter, a green colored filter, and a blue colored filter. The filter 12 rotates about an axis at a constant speed such that the color of the light transmitted to the fiber optic cable 5 cycles between red, green and blue.

An output terminal of the CCD processing circuit 14 is connected to an input terminal of the video processor 16 via the timing circuit 15. The video processor 16 outputs an analog video signal to a local monitor 20 which is located near the electronic endoscope system. The video processor 16 simultaneously outputs a digital signal through a cable 40 to a monitor at a remote location.

The operation of the CCD processing circuit 14, the timing circuit 15, and the video processor 16 are controlled by a system controller 17. Further, a peripheral driver 18 that is connected to the system controller 17 receives data from the EEPROM 8 of the endoscope 1. Character information showing the present condition of the electronic endoscope system and/or the processing of the observed image, are displayed on an operation panel (not shown) of the image processor 10, in accordance with the conditions set using a switch panel 19. Further, character information related to the current time and date, a name of a patient being observed, and other comments, are inputted using a keyboard 21. The character information inputted using the keyboard 21 is then processed by the video processor 16 and transmitted to the local monitor 20 in order to be displayed.

Figure 3:
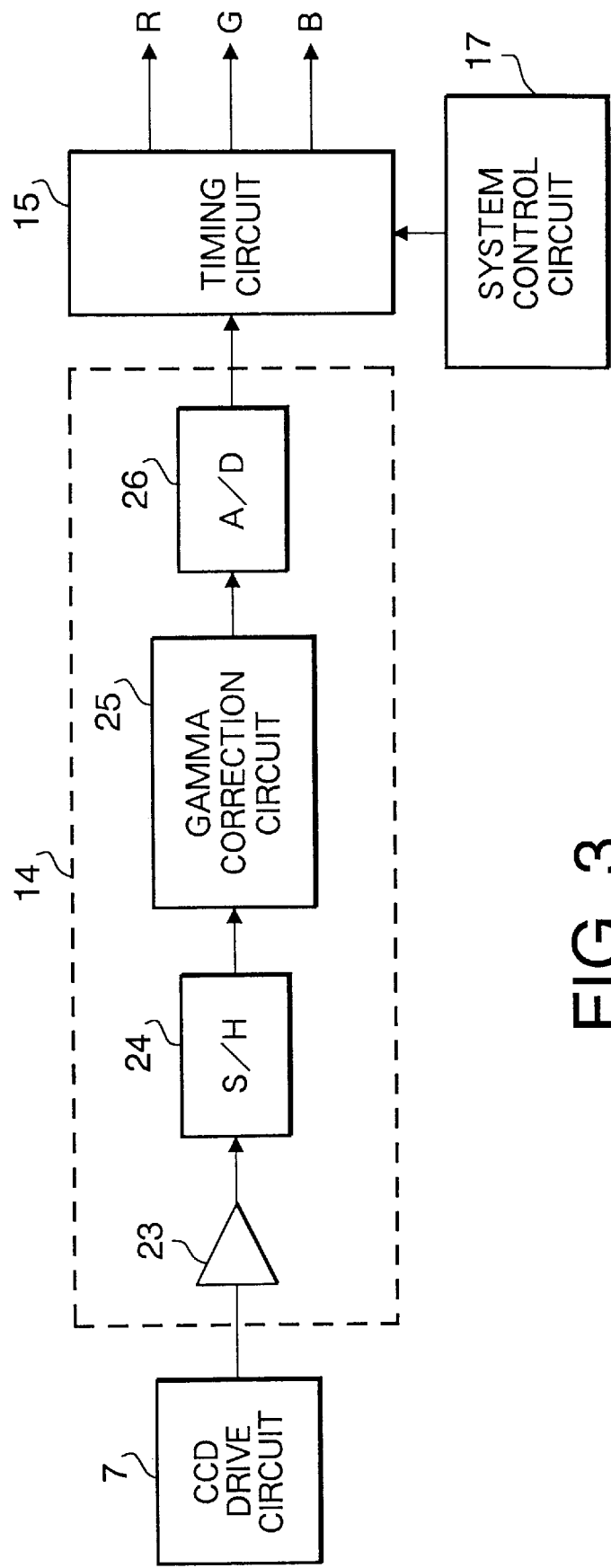
FIG. 3 shows a block diagram of a CCD processing circuit of the video processor shown in FIG. 2.

FIG. 3 shows a block diagram of the CCD processing circuit 14. The CCD processing circuit 14 includes an amplifier 23, a sample and hold circuit 24, a gamma correction circuit 25, and an A/D converter 26.

The electrical signal outputted by the CCD drive circuit 7 is amplified by the amplifier 23. The amplified signal is then sampled by the sample and hold circuit 24. Gamma correction is then applied to the signal by the gamma correction circuit 25. The gamma corrected signal is then converted from an analog signal to a digital signal by the AID converter 26. The digital signal is then outputted to the timing circuit 15.

Figure 2:
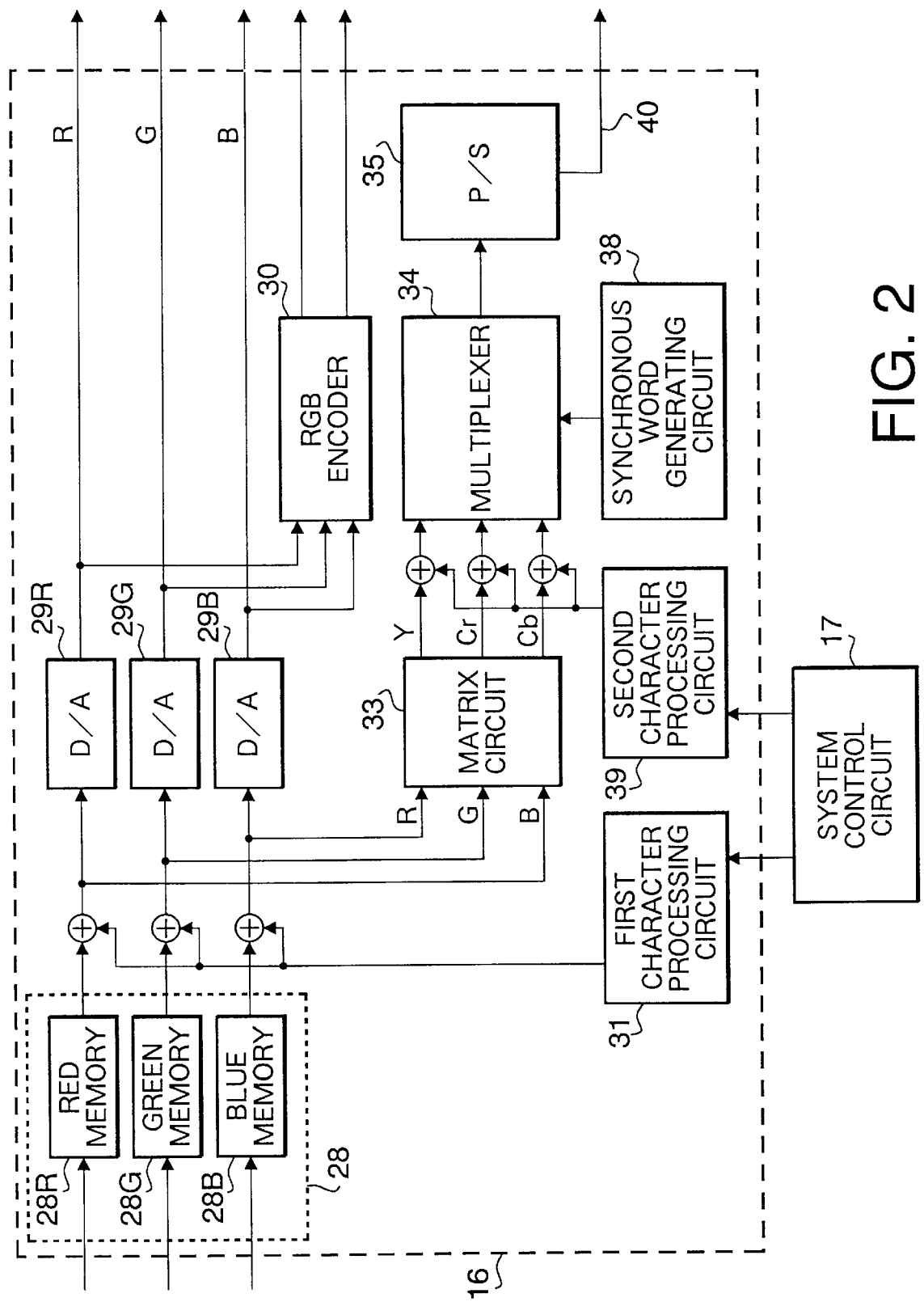
FIG. 2 shows a block diagram of a first embodiment of a video processor of the electronic endoscope system shown in FIG. 1.

FIG. 2 shows a detailed block diagram of the video processor 16.

Initially, digital image data transmitted from the CCD processing circuit 14 through the timing circuit 15 is stored in a memory 28 having three memories 28R, 28G and 28B. The system controller 17 controls the timing circuit 15 to transfer to correct color image data (i.e., red image data, green image data, and blue image data) to a corresponding memory. The memory 28R stores the red image data, the memory 28G stores the green image data, and the memory 28B stores the blue image data. The stored data is read out of the three memories 28R, 28G and 28B and is transmitted to three D/A converters 29R, 290 and 29B, respectively. The data is D/A converted by the D/A converters 29R, 29G and 29B, and analog RGB signals are outputted, respectively. Simultaneously, the outputted analog RGB signals are sent to an RGB encoder 30 which converts the RGB signals to a composite video signal and an S video signal.

Character information inputted by the keyboard 31 and processed by the system controller 17 is further processed by a first character processing unit 31. The first character processing unit 31 outputs digital character information which is added to the digital RGB signals read out of the memories 28R, 28G and 28B. Therefore, the analog RGB signals include the character information input using the keyboard 21.

As further shown in FIG. 2, the digital RGB signals are also input to a matrix circuit 33. The matrix circuit 33 samples the digital RGB signals (which include the character information) at 27 MHz to output a brightness signal Y, and two color difference signals Cr (where Cr=R−Y) and Cb (where Cb=B−Y). Further data related to an operation of the electronic endoscope system and the processing of the observed image are processed by the second character processing circuit 39, such that character data is generated. The generated character data is then combined with each of the Y, Cr and Cb signals. The Y, Cr and Cb signals (which include the generated character data) are then multiplexed by a multiplexer 34 with a synchroword signal generated by a synchronous word signal generator 38.

The multiplexer 34 samples the Y signal at 13.5 MHz and samples each of the Cr and Cb signals at 6.75 MHz in the order Cb, Y, Cr, Y, Cb, Y . . . etc. Further, for one line of image data 720 samples of the Y signal and 360 samples for each of Cr and Cb signals are taken for a total of 1440 samples.

FIG. 4A shows an example of an analog signal outputted by the image processor to the local monitor 20. FIG. 4B shows the corresponding digital data outputted to the remote location. The data represented by the numeral 200 represents the synchroword, and the data represented by the numeral 201 represents the 1440 samples of serial data Cb, Y, Cr, Y, Cb, Y etc. described above. Further, the numeral 202 represents the blanking period of the picture signals.

The data outputted by the multiplexer is parallel data. In order to transmit the parallel data to a remote location a cable having a number of lines equal to the number of bits plus one (for the clock signal) would be required. Therefore, if the parallel data is converted to serial data, the number of lines required in the transmission cable can be reduced.

Figure 5:
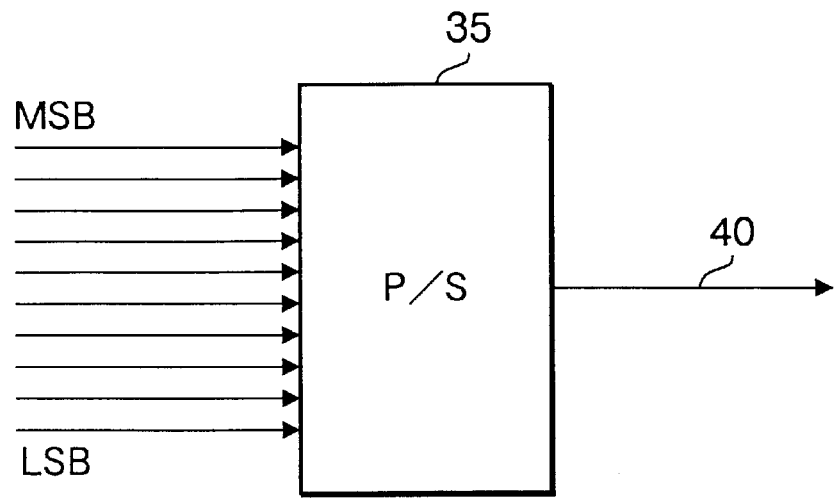
FIG. 5 shows a schematic diagram of a parallel/serial converter of the video processor shown in FIG. 2.

The multiplexer 34 therefore outputs the parallel data to a parallel/serial converter 35. As shown in FIG. 5, the parallel/serial converter 35 converts the multi-bit parallel data to serial data. The serial data is transmitted (starting with the lowest significant bit) along the cable 40 to a remote monitor 53 at a transmission rate of 270 Mb/s, which is equivalent to ten times the clock frequency of 27 MHz.

Figure 6:
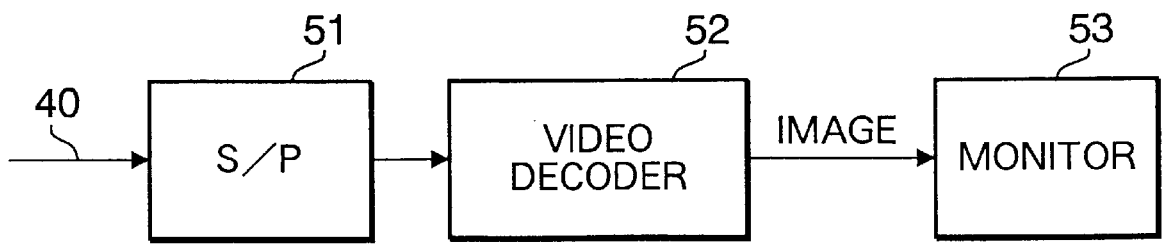
FIG. 6 shows a schematic diagram of a monitor and data processor at a re mote location used to display an image detected by the electronic endoscope system, shown in FIG. 1.

At the remote location as shown in FIG. 6, a serial/parallel converter 51 converts the serial data to parallel data. The digital data is then decoded by a video decoder 52, and an image signal is transmitted to the remote monitor 53.

Figure 7:
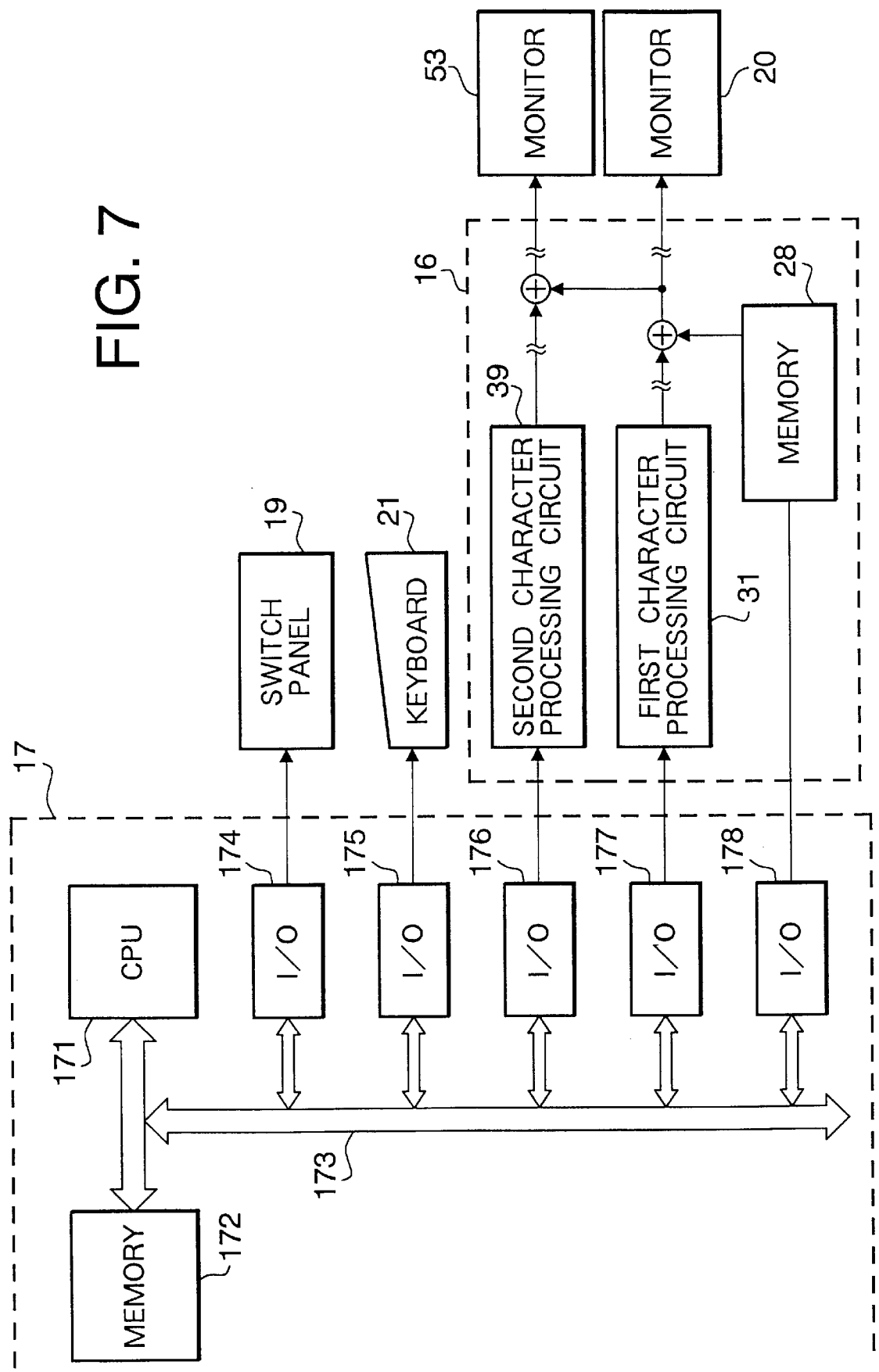
FIG. 7 shows a block diagram of a system controller used in the video processor shown in FIG. 2.

FIG. 7 shows a portion of the system controller 17 related to the processing of character information, and the other associated hardware.

As shown in FIG. 7, the system controller 17 has a CPU 171, a memory 172, a system bus 173 and a plurality of input/output ports 174 through 178 (hereinafter referred to as I/O ports). The panel switch 19 is connected to the first I/0 port 174, while the keyboard 21 is connected to the second I/O port 175. Further, the second character processing circuit 39 is connected to the I/O port 176 and the first character processing circuit 31 is connected to the I/O port 177. The I/O port 178 is used to control various components of the video processor 16 (such as the memory 28 as shown in FIG. 7) that are related to the processing of the image data.

Figure 8:
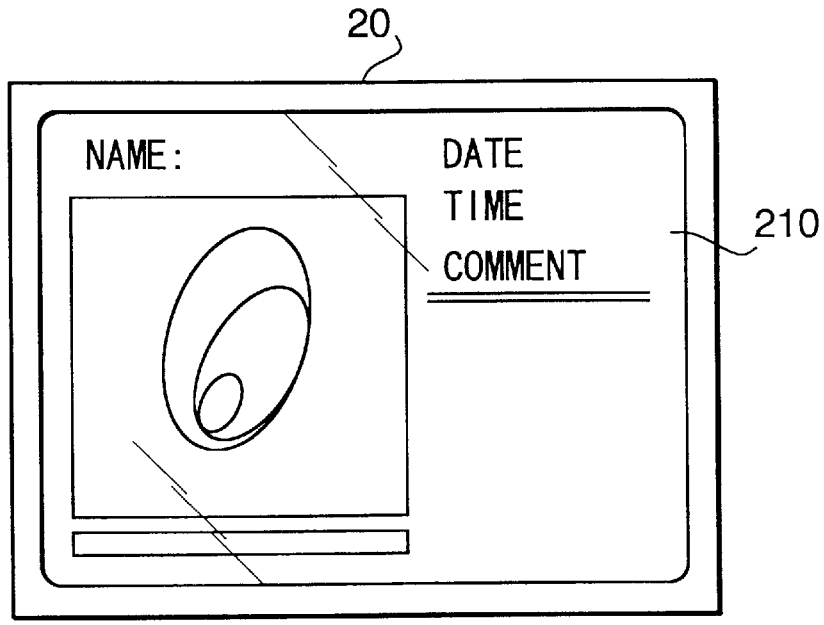
FIG. 8 shows an example of an image displayed on a monitor located near the electronic endoscope system shown in FIG. 1.

As described above, and show in FIG. 7, the first character processing circuit 31 outputs character data which is combined with the image data and sent to the local monitor 20. As shown in FIG. 8, numeral 210 represents the character data outputted by first character processing circuit 31 that is related to the current date and time, the name of the patient, and any comments.

Figure 9:
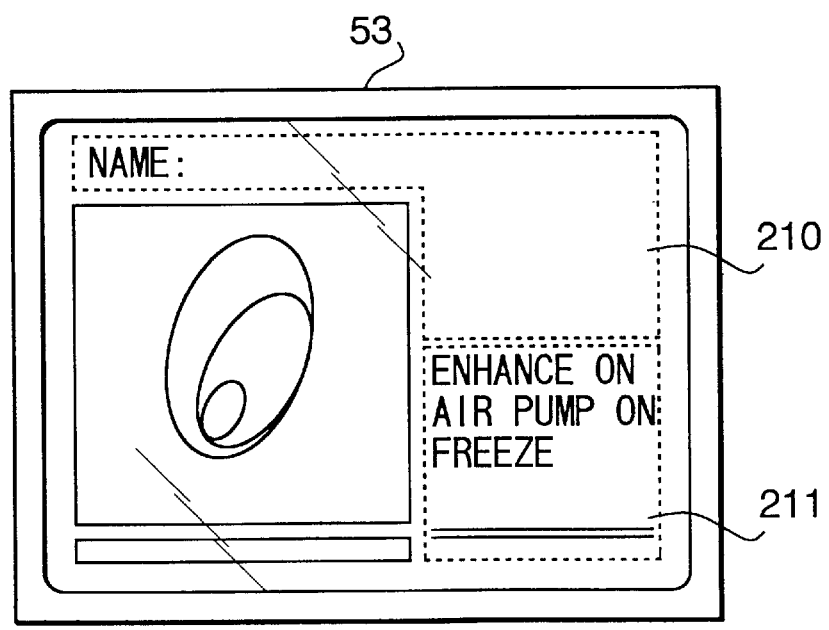
FIG. 9 shows an example of an image displayed on a monitor at a remote location from the electronic endoscope system shown in FIG. 1.

Further, as shown in FIG. 7, the second character processing circuit 39 outputs character data related to an operation of the video processor 16, and the processing of the image data. As shown in FIG. 9, this additional information which is represented by numeral 211 is displayed on the remote monitor 53.

As described above, by transmitting the image signal as a digital signal through the cable 40 to the remote monitor 53, a high quality image can be reproduced without any loss of quality due to signal loss. Further, as the data is transmitted serially, only a cable having a single data line is required for transmitting the data. This reduces the cost of the hardware rewired to transmit the data.

Furthermore, by utilizing the second character Pr ceasing circuit 39, the operation condition of the video processor and the processing condition of the image can be transmitted to the remote monitor in addition to the data normally displayed on the monitor. This allows an operator at the remote location to have as much information as possible about the operation of the electronic endoscope system.

Figure 10:
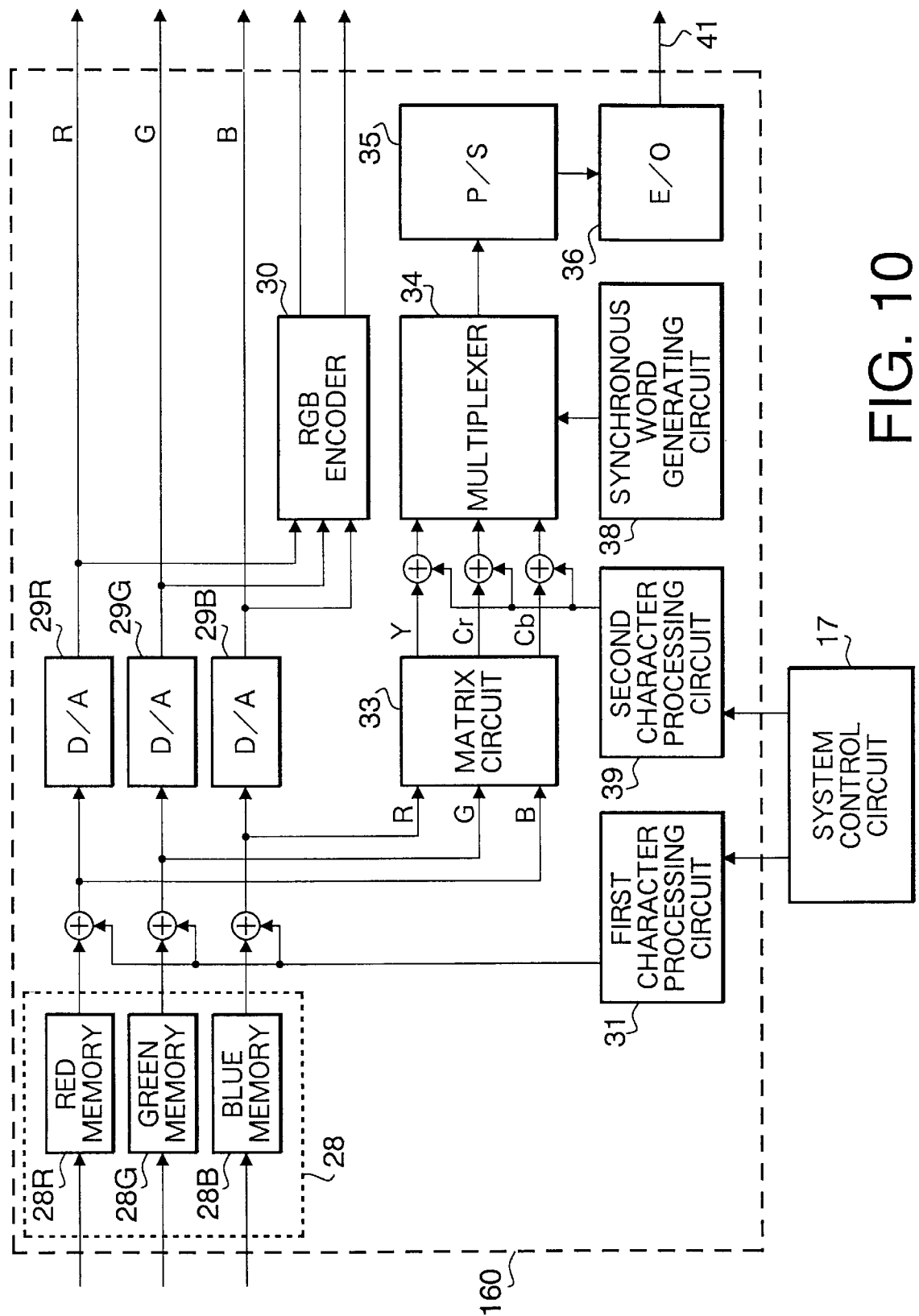
FIG. 10 shows a block diagram of a second embodiment of a video processor of the electronic endoscope system shown in FIG. 1.

FIG. 10 shows a block diagram of a video processor 160 according to a second embodiment of the electronic endoscope system shown in FIG. 1.

The video processor 160 is similar to the video processor 16, with the common parts having the same reference numerals. However, as shown in FIG. 10, the serial data output by the parallel/serial converter 35 is converted to an optical signal by an electrical to optical converter 36. The optical signal is then outputted to the remote monitor 53.

Thus, according to the second embodiment of the present invention, the distance of the remote monitor 53 from the electronic endoscope system can be increased substantially without any loss in image quality. Further, there is an additional advantage of electrical isolation of the cable 41.

Figure 11:
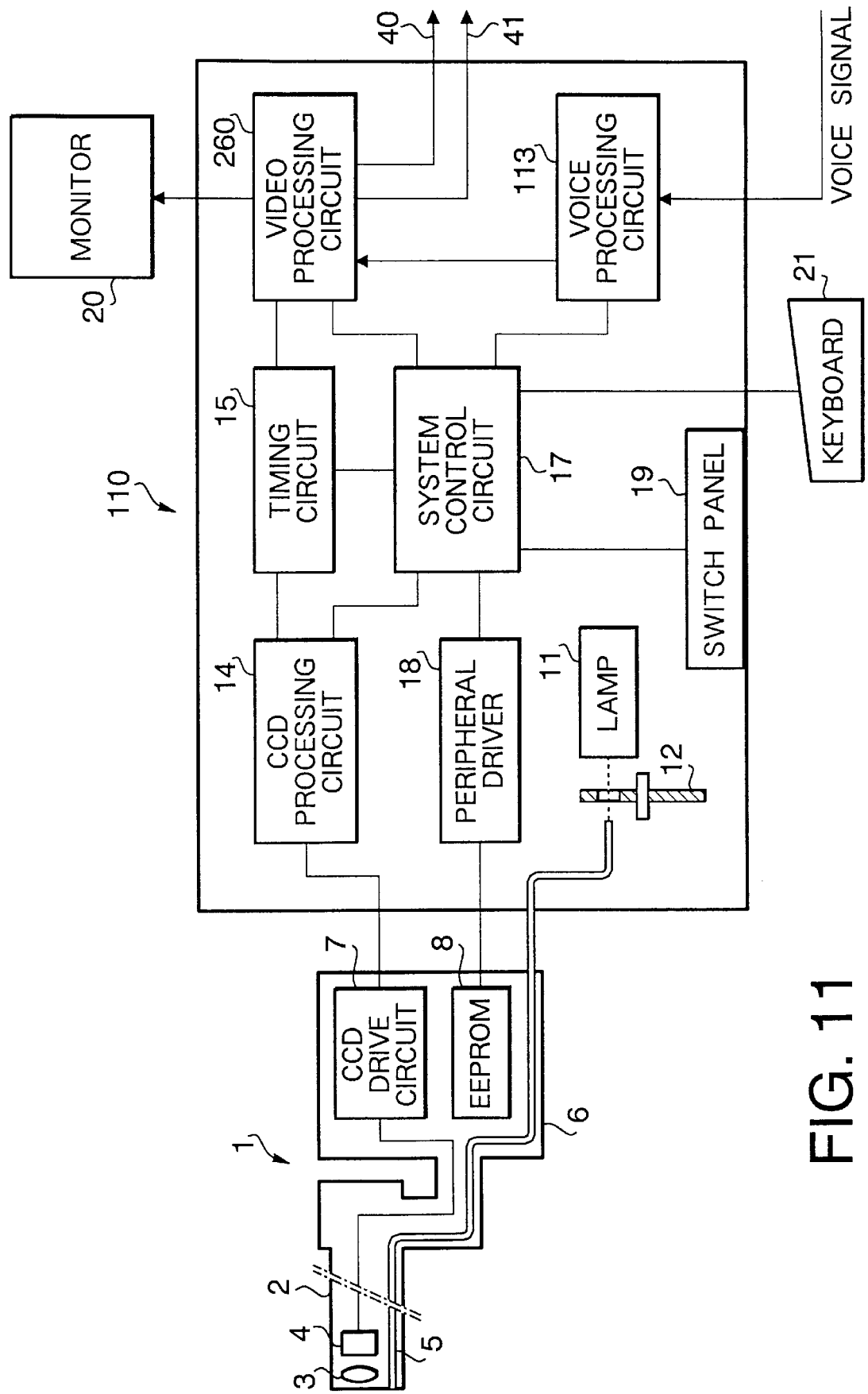
FIG. 11 shows a schematic diagram of a electronic endoscope system according to a third embodiment of the present invention.

FIG. 11 shows a block diagram of a third embodiment of the electronic endoscope system according to the present invention. In the third embodiment, the electronic endoscope system has an endoscope 1 and an image processor 110. The image processor 110 is similar to the image processor 10 described above in the first embodiment, but includes the video processor 260 and the voice processing circuit 113, instead of the video processor 16.

Figure 13:
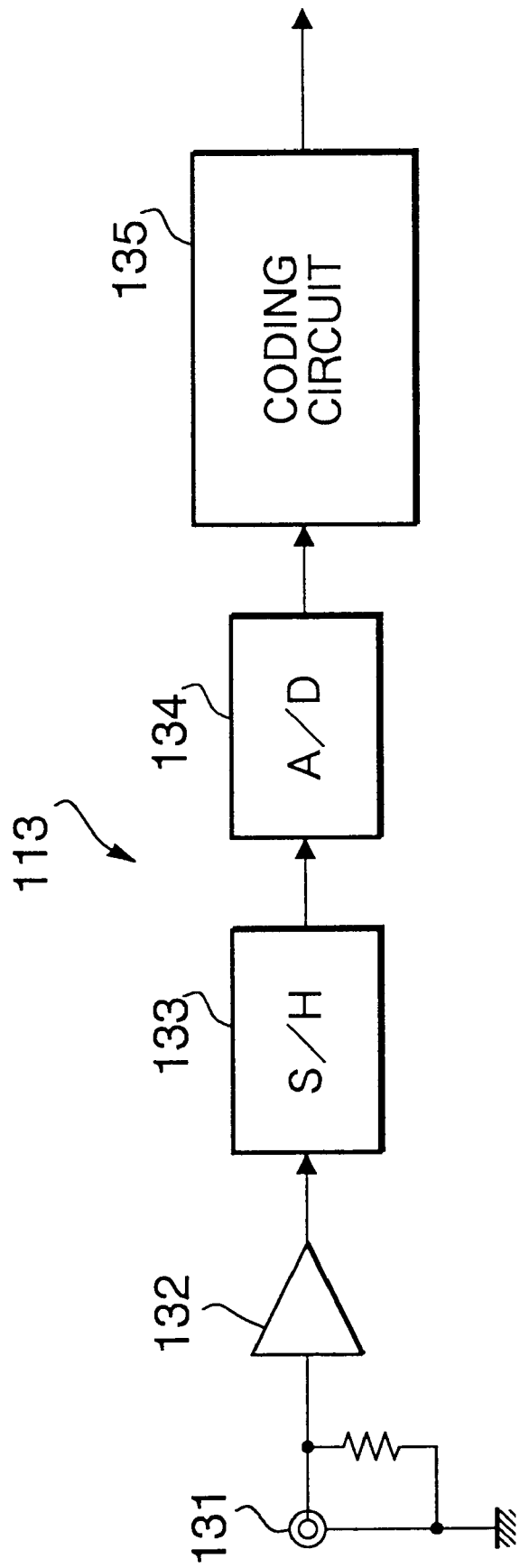
FIG. 13 shows a schematic diagram of a voice processing circuit of the electronic endoscope system shown in FIG. 11.

FIG. 13 shows a schematic diagram of the voice processing circuit 113. A Microphone 131 converts a received voice signal to an electrical signal. The electrical signal is amplified by amplifier 132, and sampled by the sample and hold circuit 133. The analog signal is then converted to a digital signal by the A/D converter 134. The digital signal is then coded by the coding circuit 135, and outputted to the video processor 260. The operation of the voice processing circuit 113 is controlled by the system controller 17 through the I/O port 176, as shown in FIG. 18.

Figure 12:
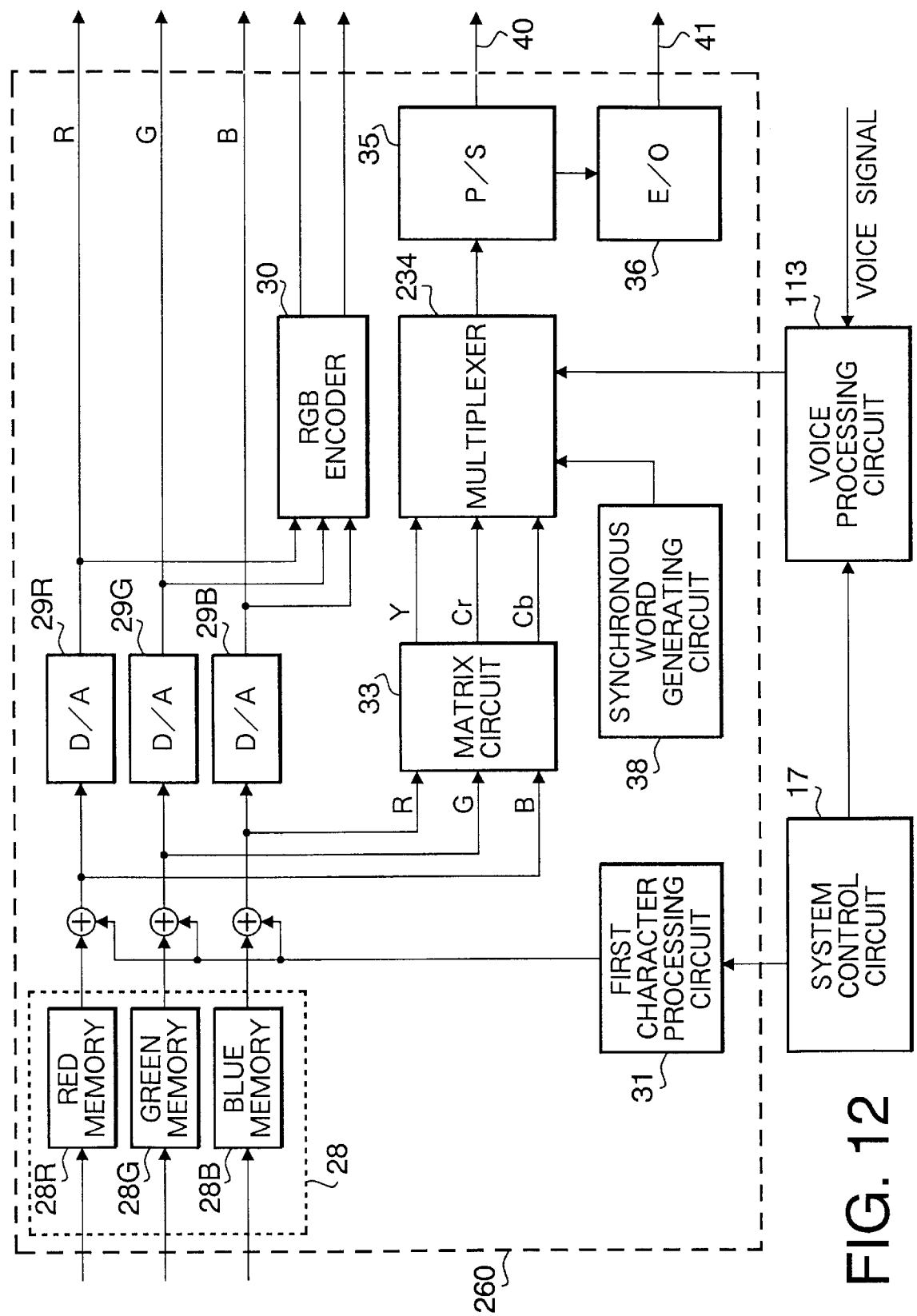
FIG. 12 shows a block diagram of a video processor of the electronic endoscope system shown in FIG. 11.

FIG. 12 shows a block diagram of the video processor 260. The video processor 260 is similar to the video processor 16 described above, with the common parts having the same reference numerals. As shown in FIG. 12, a multiplexer 234 multiplexes the Y, Cr and Cb signals with the coded voice signal outputted from the coding circuit 135, and the synchroword signal. The multiplexed signal is converted to a serial signal by the parallel to serial converter 35 and then outputted as an electrical signal along the cable 40. The serial signal is also converted to an optical signal by the electrical to optical converter 36 and then outputted along the optical cable 41.

Figure 14A:
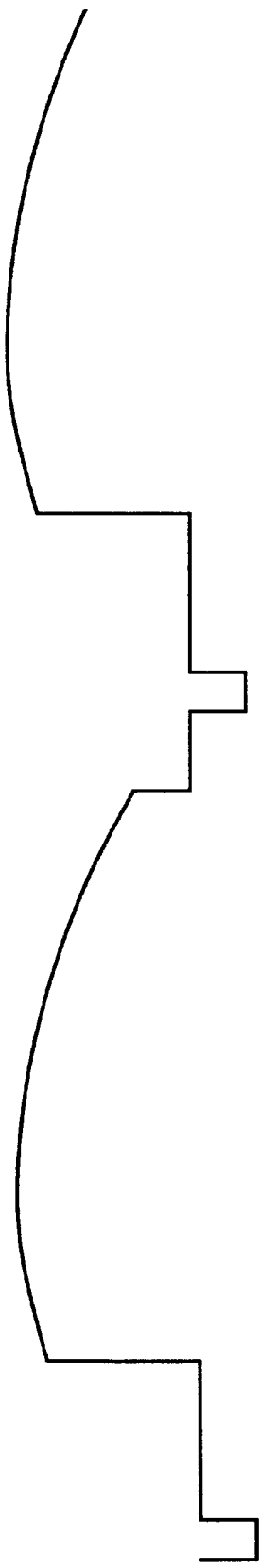
FIG. 14A shows a timing diagram of a transmission of an analog image from the video processor shown in FIG. 12 to a local monitor, when no voice data is sent.
Figure 14B:
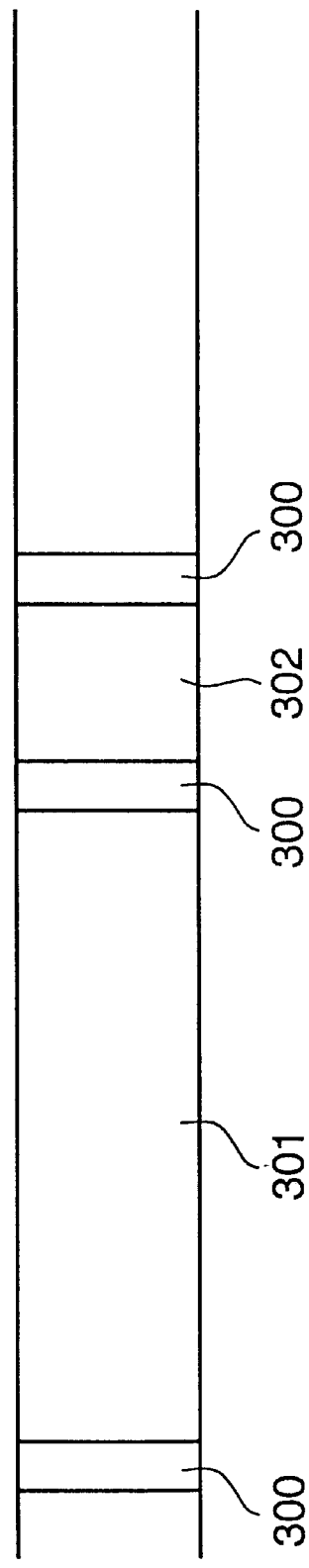
FIG. 14B shows a timing diagram of a transmission of serial image data from the video processor shown in FIG. 12 to a remote monitor when no voice data is sent.

FIG. 14A shows an example of an analog signal output by the image processor to the local monitor 20, when no voice data is transmitted. FIG. 14B shows the corresponding digital data outputted to the remote location. The data represented by the numeral 300 is the synchroword, and the data represented by the numeral 301 are the 1440 samples of serial data Cb, Y, Cr, Y, Cb, Y etc., described above. Further, the numeral 302 represents the blanking period of the picture signals.

Figure 15A:
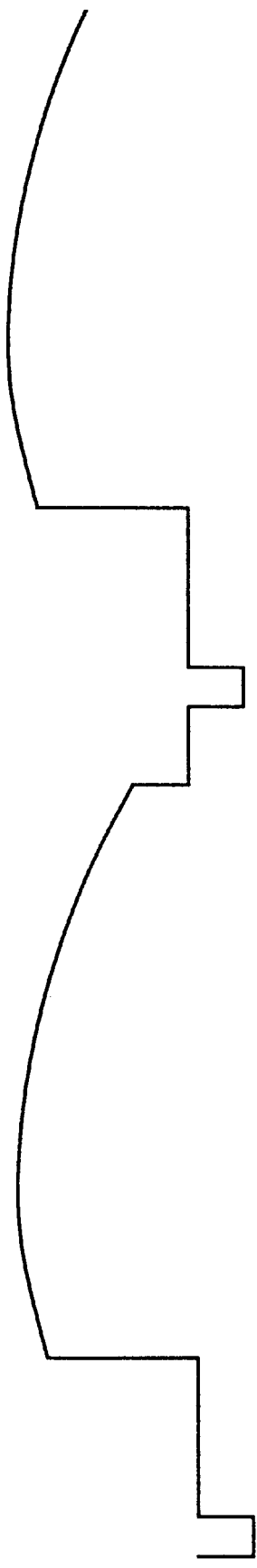
FIG. 15A shows a timing diagram of a transmission of an analog image from the video processor shown in FIG. 12 to a local monitor, when voice data is sent.
Figure 15B:
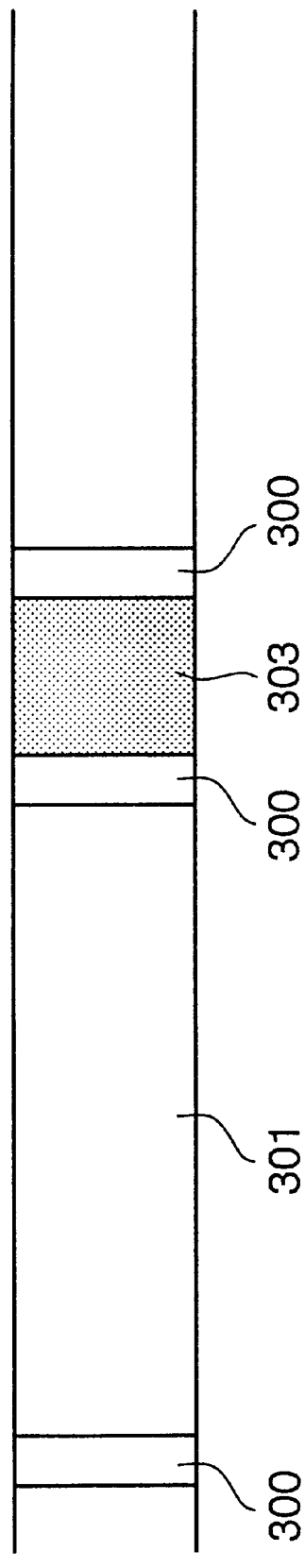
FIG. 15B shows a timing diagram of a transmission of serial image data from the video processor shown in FIG. 12 to a remote monitor when voice data is sent.

FIG. 15A shows an example of an analog signal output by the image processor to the local monitor 20, when voice data is transmitted. FIG. 15B shows the corresponding digital data outputted to the remote location. In this case the voice data, which is represented by numeral 303 is inserted into the blanking period between the synchrowords which denote the end of one line of image data and the start of the subsequent line of image data.

Thus, as shown in FIGS. 14A through 15B, the voice data is transmitted along with the image data to the remote monitor 53.

Figure 16:
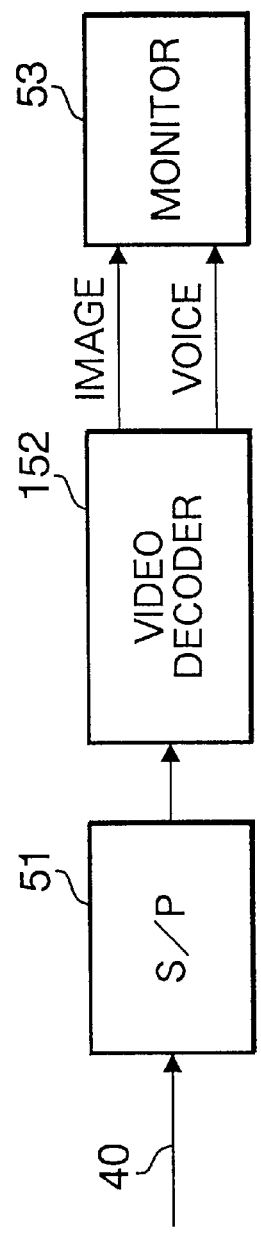
FIG. 16 shows a schematic diagram of a monitor and data processor at a remote location used to display an image detected by the electronic endoscope system shown in FIG. 11 using an electrical cable.

Then, as shown in FIG. 16, the image signal which is transmitted to the remote monitor 53 along the cable 40, is converted to a parallel signal by the serial to parallel converter 51. The converted signal is then processed by a video decoder 152 in order to decode the image and voice signal. The image and voice signal are then sent to the remote monitor 53. In this third embodiment, the monitor 53 includes a speaker for reproducing the voice signal at the remote location. However, a separate speaker may be employed.

Figure 17:
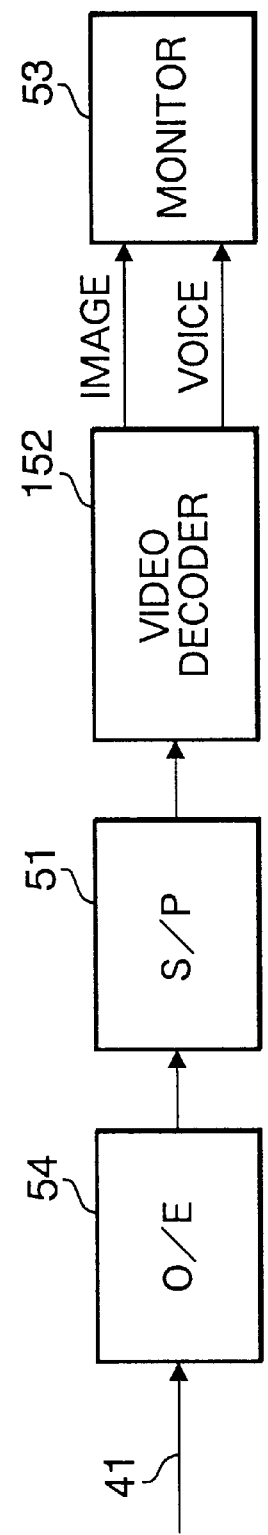
FIG. 17 shows a schematic diagram of a monitor and data processor at a remote location used to display an image detected by the electronic endoscope system shown in FIG. 11 using an optical cable.

Alternatively, if the image signal is transmitted to the remote monitor along the optical cable 41, the optical signal is first converted to an electrical signal by the optical to electrical converter 54, as shown in FIG. 17. Then the electrical signal is processed and decoded as described above.

Thus, as described above, a voice processing circuit may be used in conjunction with the first character processing circuit 31 in order that voice or other audio signals may be transmitted from the electronic endoscope system to the remote monitor. This has the added advantage that other conditions (such as verbal comments) in addition to those concerning the operation of the electronic endoscope system, may also be transmitted to the remote location. Further, the operation of the electronic endoscope system can be made easier, since additional commands or information can be verbally instructed.

The present disclosure relates to subject matter contained in Japanese Patent Application No. HEI 7-017585 filed on Feb. 6, 1995, and Japanese Patent Application No. HEI 7-155835 filed on Jun. 22, 1995, which are expressly incorporated herein by reference in its entireties.

What is claimed is:

1. An electronic endoscope system comprising:
   means for detecting an image and outputting an electrical image signal;
   means for converting said electrical image signal, wherein said image detecting means outputs said electrical image signal to said means for converting and said means for converting converts said electrical image signal to an analog motion video signal and a digital motion video signal;
   means for inputting an information signal and outputting character data;
   means for combining said digital motion video signal with said character data, to form a combined digital information signal including both said digital motion video signal and said character data;
   means for serially outputting said combined digital information signal;
   means for displaying said electrical image signal as motion video in accordance with said serially outputted combined digital information signal; and
   means for reproducing said information signal in accordance with said serially outputted combined digital information signal.

2. The electronic endoscope system according to claim 1, wherein:
   said means for detecting an image outputs a real-time electrical image signal;
   said means for converting converts said real-time electrical image signal to a real-time analog motion video signal and a real-time digital motion video signal;
   said means for combining comprises a multiplexer that multiplexes said real-time digital motion video signal with said character data, to form a multiplexed combined digital information signal including both said digital motion video signal and said character data;
   said means for serially outputting serially transmits said multiplexed combined digital information signal in real time;
   said means for displaying displays motion video of said image, without intervention of a storage device between said serial outputting means and said displaying means, in accordance with said serially outputted multiplexed combined digital information signal; and
   said means for reproducing reproduces said information signal by extracting said information signal from said serially outputted multiplexed combined digital information signal.

3. An electronic endoscope system comprising:
   means for detecting an image and outputting an electrical image signal representative of said image;

means for converting said electrical image signal, wherein said means for detecting and outputting outputs said electrical image signal to said means for converting, and said means for converting converts said electrical image signal to an analog video signal and a digital video signal;

means for processing character data according to information received from said converting means;

means for combining said character data with said digital video signal, whereby said information received from said converting means is combined with said digital video signal;

means for serially outputting said digital video signal;

first means for displaying said image in accordance with said analog video signal; and second means for displaying said image in accordance with said serially outputted digital video signal.

4. The electronic endoscope system according to claim 3, further comprising:

means for processing character data; and means for combining said character data with said analog video signal.

5. The electronic endoscope system according to claim 4, said character processing means comprising a keyboard for inputting said character data.

6. The electronic endoscope system according to claim 3, further comprising:

means for converting said serially outputted digital video signal to an optical signal; and means for transmitting said optical signal to said second display means.

7. The electronic endoscope system according to claim 3, further comprising:

means for converting an analog audio signal to a digital audio signal; and means for combining said digital audio signal with said digital video signal.

8. The electronic endoscope system according to claim 3, wherein said analog video signal includes a composite video signal and an S video signal.

9. An electronic endoscope system wherein an image detected by an imaging device is separated into analog red, green and blue image signals, and the analog red, green and blue image signals are further processed and outputted to a monitor, said electronic endoscope system comprising:

means for outputting an analog composite video signal and an S video signal to said monitor;

means for converting said analog red, green and blue image signals into a digital video signal;

character processing means receiving information from said converting means wherein said information from said converting means is combined with said digital video signal; and means for serially outputting said digital video signal.

10. The electronic endoscope system according to claim 9, further comprising:

means for generating character information; and means for combining said character information with said digital video signal.

11. The electronic endoscope system according to claim 9, further comprising:

means for converting an analog audio signal to a digital audio signal; and means for combining said digital audio signal with said digital video signal.

12. An electronic endoscope system comprising:

means for detecting an image and outputting an electrical image signal;

means for converting said electrical image signal, wherein said image detecting and outputting means outputs said electrical image signal to said means for converting and said means for converting converts said electrical image signal to an analog video signal and a digital video signal;

means for converting an analog audio signal to a digital audio signal;

means for combining said digital video signal with said digital audio signal, to form a digital information signal;

means for serially outputting said digital information signal;

means for displaying said image in accordance with said serially outputted digital information signal; and means for reproducing said analog audio signal in accordance with said serially outputted digital information signal.

13. The electronic endoscope system according to claim 12, further comprising:

means for generating character information; and means for combining said character information with said digital information signal.

14. The electronic endoscope system according to claim 13, further comprising: means for inputting data, wherein said character information is generated in accordance with data inputted by said means for inputting data.

15. The electronic endoscope system according to claim 12, further comprising:

means for converting said serial digital information signal to an optical signal; and means for transmitting said optical signal to said display means.

16. An electronic endoscope system comprising:

means for detecting an image and outputting an electrical image signal;

means for converting said electrical image signal, wherein said image detecting means outputs said electrical image to said means for converting and said means for converting converts said electrical image signal to an analog video signal and a digital video signal;

means for inputting an information signal, comprising means for receiving an analog audio signal and means for converting said analog audio signal to a digital audio signal;

means for combining said digital video signal with said information signal inputted by said means for inputting, to form a digital information signal;

means for serially outputting said digital information signal;

means for displaying said image in accordance with said serially outputted digital information signal; and means for reproducing said information signal in accordance with said serially outputted digital information signal.

17. An electronic endoscope system comprising:

an image detector for detecting an image and outputting an electrical image signal;

a converting device that converts the electrical image signal to an analog video signal and a digital video signal;

an information signal input device for inputting an information signal, including a character processor that receives, from said converting device, data representative of an operation of said converting device, and adds character data to the information signal in accordance with the received data from said converting device;

a signal combining device that combines the digital video signal with the information signal to form a digital information signal;

a serial output device for serially outputting the digital information signal;

a display for displaying the image in accordance with the serially outputted digital information signal; and a reproducing device for reproducing the information signal in accordance with the serially outputted digital information signal.

18. The electronic endoscope system according to claim 17, wherein said data representative of an operation of the converting device includes data concerning the operation of the electronic endoscope system.

19. The electronic endoscope system according to claim 17, wherein said data representative of an operation of the converting device including an operation condition of a video processor and a processing condition of said image.

20. An electronic endoscope system comprising:

an image detector for detecting an image and outputting an electrical image signal;

a converting device that converts the electrical image signal to an analog video signal and a digital video signal;

an analog-to-digital convertor for converting an analog audio signal to a digital audio signal;

a signal combining device that combines the digital video signal into the digital audio signal to form a digital information signal;

a serial output device for serially outputting the digital video signal;

a first display for displaying the image in accordance with the analog video signal; and a second display for displaying the image in accordance with said serially outputted digital video signal.

21. An electronic endoscope system wherein an image detected by an imaging device is separated into analog red, green and blue image signals, and the analog red, green and blue image signals are further processed and outputted to a monitor, said electronic endoscope system comprising:

an output device that outputs an analog composite video signal and an S video signal to said monitor;

a first converting device that converts the analog red, green and blue image signals into a digital video signal;

a second converting device that converts an analog audio signal to a digital audio signal;

a signal combining device that combines the digital audio signal into the digital video signal;

a serial output device for serially outputting the digital video signal.

22. An electronic endoscope system comprising:

an image detector for detecting images and outputting image signals;

a converting device that converts said image signals to a real-time analog motion video signal and a real-time digital motion video signal;

an information signal input device for inputting a information signal;

a signal combining device that combines said real-time digital motion video signal with said information signal to form a real-time digital information signal;

a serial output device for serially outputting said real-time digital information signal;

a display for displaying said image signals as real-time motion video in accordance with said serially outputted digital information signal; and a reproducing device for reproducing said information signal in accordance with said serially outputted digital information signal.

23. The electronic endoscope system according to claim 22, wherein:

said an image detector outputs real-time image signals;

said converting device converts said real-time image signals to a real-time analog motion video signal and a real-time digital motion video signal;

said signal combining device comprises multiplexer that multiplexes said real-time digital motion video signal with said information signal to form a multiplexed real-time digital information signal;

said serial output device serially transmits said multiplexed real-time digital information signal;

said display displays said images as motion video, without intervention of a storage device between said serial output device and said display, in accordance with said serially outputted multiplexed real-time digital information signal; and said reproducing device reproduces said information signal by extracting said information signal from said serially outputted multiplexed real-time digital information signal.

* * * * *